United States Patent
Kaul

Patent Number: 5,145,390
Date of Patent: Sep. 8, 1992

[54] APPARATUS HAVING A MECHANISM FOR THE ACCEPTANCE OF AN ELECTRICAL CONDUCTOR

[75] Inventor: Karlheinz Kaul, Uttenreuth, Fed. Rep. of Germany

[73] Assignee: Siemens Aktiengesellschaft, Munich, Fed. Rep. of Germany

[21] Appl. No.: 710,468

[22] Filed: Jun. 5, 1991

[30] Foreign Application Priority Data

Jun. 19, 1990 [DE] Fed. Rep. of Germany ....... 4019513

[51] Int. Cl.⁵ ............................................ H01R 39/02
[52] U.S. Cl. .................................. 439/164; 242/100.1; 439/13
[58] Field of Search ................. 439/13, 164; 242/86.1, 242/700.1

[56] References Cited

U.S. PATENT DOCUMENTS

| | | |
|---|---|---|
| 1,868,409 | 7/1932 | Crispen . |
| 2,518,071 | 8/1950 | Rushworth . |
| 3,412,951 | 11/1968 | Ober . |

FOREIGN PATENT DOCUMENTS

| | | | |
|---|---|---|---|
| 156370 | 7/1952 | Australia ........................ 242/100.1 |
| 0071875 | 2/1983 | European Pat. Off. .............. 439/13 |
| 2624422 | 12/1977 | Fed. Rep. of Germany . |
| 7811922 | 8/1978 | Fed. Rep. of Germany . |
| 2828686 | 1/1979 | Fed. Rep. of Germany . |
| 2747126 | 4/1979 | Fed. Rep. of Germany ........ 439/13 |
| 2621308 | 8/1980 | Fed. Rep. of Germany . |
| 2821319 | 10/1980 | Fed. Rep. of Germany . |
| 1766053 | 2/1984 | Fed. Rep. of Germany . |
| 8909486 | 12/1989 | Fed. Rep. of Germany . |
| 2741240 | 10/1990 | Fed. Rep. of Germany . |

*Primary Examiner*—Eugene F. Desmond
*Attorney, Agent, or Firm*—Hill, Van Santen, Steadman & Simpson

[57] ABSTRACT

An apparatus having a stationary part and a movable part, with an electrical conductor running between one or more components on each part, includes a mechanism for winding and unwinding the electrical conductor as the movable part is moved relative to the stationary part. The mechanism includes a rotatable drum onto which, and from which, both the electrical conductor and a cable can be wound or unwound in opposite winding directions. By exerting a tensile force on the conductor, the conductor can be unwound from the drum while the cable is being wound onto the drum. Conversely, the cable can be unwound from the drum while the conductor is being wound onto the drum, given a tensile force on the cable. If both the cable and the conductor are mechanically connected to the movable part, the forces acting on the movable part during winding or unwinding of the conductor balance substantially to zero.

8 Claims, 2 Drawing Sheets

APPARATUS HAVING A MECHANISM FOR THE ACCEPTANCE OF AN ELECTRICAL CONDUCTOR

BACKGROUND OF THE INVENTION

1. Field of the Invention

The present invention is directed to a mechanism for the acceptance of an electrical conductor, and in particular to such a mechanism for winding and unwinding an electrical conductor, connected between a stationary part and a movable part, as the movable part is moved relative to the stationary part.

2. Description of the Prior Art

German Utility Model 89 09 486 discloses a portable x-ray examination apparatus having two parts which are adjustable relative to each other, and a mechanism for accepting an electrical conductor, extending between the two parts, as the parts are moved relative to each other. The conductor provides an electrical connection between electrical components respectively carried on the two parts. The mechanism has an outer, hollow, cylindrical drum which is rotatably seated around an inner, stationary, hollow, cylindrical drum. The exterior surface of each drum has an opening through which the conductor is conducted. A first lengthwise region of the conductor is conducted through the opening of the exterior surface of the inner drum, in the region between the drums and is secured to the drums so that it is wound onto, or wound off of, the inner drum upon rotation of the outer drum. A second lengthwise region of the conductor is conducted through the opening of the exterior surface of the outer drum. Upon rotation of the outer drum, this second region is wound onto, or wound off of, the exterior surface of the outer drum. A guide is provided through which the second region of the conductor is conducted to the exterior surface of the outer drum. Upon adjustment of the movable units relative to each other, a tensile or compressive force is exerted on the conductor, the outer drum rotating as a result thereof and thereby effecting winding or unwinding of the conductor.

SUMMARY OF THE INVENTION

It is an object of the present invention to provide an apparatus for reliably winding and unwinding a conductor without conductor loops arising.

The above object is achieved in accordance with the principles of the present invention in an apparatus for accepting an electrical conductor having a rotatable drum onto which and from which both a conductor and a cable can be wound and unwound in opposite winding directions. As the conductor, for example, is being wound onto the drum, the cable is being unwound, and vice versa.

An advantage of the mechanism disclosed herein is that guides for guiding the conductor to the rotatable drum can be eliminated, so that the manufacturing costs and assembly outlay are reduced. Moreover, in the apparatus disclosed herein the conductor is not required to transmit any forces which act as compressive forces on the conductor to cause rotation of the drum for winding the conductor. In the mechanism disclosed herein, the force for rotating a drum to wind the conductor is transmitted through the cable. Since the conductor does not have to withstand significant compressive forces without buckling, the conductor can be more flexible than in known structures, so that the cross-section moduli of the conductor are reduced. Winding or unwinding of the conductor is thus achieved by forces which substantially balance to zero.

Preferably the cable is wound onto a first width region of the drum and the conductor can be wound onto a second width region of the drum.

If the diameter of the cable is equal to the diameter of the conductor, the wound or unwound length of the cable will correspond to the wound or unwound length of the conductor. A uniform winding or unwinding with neutral (i.e., balanced to zero) forces is thus insured.

Winding and unwinding with neutral forces can still be achieved if the diameter of the cable is less than the diameter of the conductor by providing the first width region of the drum, onto which the cable is to be wound, with a helical channel, which receives the cable, and which has a pitch corresponding to the diameter of the conductor (or the height of a turn of the conductor on the drum). The cable can thus be made thinner than the diameter, or height, of the conductor, and thereby eliminate weight.

The overall drum is preferably formed by an outer, hollow, cylindrical drum, rotatably seated around an inner, stationary, hollow, cylindrical drum. The respective exterior surfaces of the inner and outer drums each have an opening. A first lengthwise region of the conductor is conducted through the interior of the inner drum and through the opening in the exterior surface thereof and into the region between the inner and outer drums. The first region of the conductor is mechanically fixed to the drums, so that it is wound onto or off of the inner drum upon rotation of the outer drum. A second lengthwise region of the conductor is conducted through the opening of the exterior surface of the outer drum to the aforementioned second width region of the outer drum. The conductor can be wound from the outer drum given the exertion of a tensile force on the conductor, and the cable can be wound onto the outer drum given the exertion of a tensile force on the cable. Such a mechanism has a compact structure. No compressive, tensile or torsional forces are exerted on the first region of the conductor when winding or unwinding the second region of the conductor. Such forces can possibly result in damage to the conductor. Mechanical stress on the conductor is reduced.

The apparatus in which the mechanism for accepting the electrical conductor is contained may be an apparatus having first and second parts, with the second part being movable relative to the first part. The first and second parts carry respective electrical components which are connected by the conductor. The apparatus may, for example, be an x-ray examination unit wherein the first part is the base or holder for a C-shaped arc which carries, at its opposite free ends, an x-radiator and a radiation receiver. The arc can be moved through the holder along its circumference. The cable is mechanically secured to one end of the arc, and the conductor is secured to the other end of the arc. Winding and unwinding of the conductor onto and from the aforementioned mechanism can be achieved with neutral force as the arc moves along its circumference.

Preferably the cable is mechanically attached to one end of the arc by means of a spring element. As a result, a tensile force is exerted on the conductor, so that the conductor can be wound tightly upon itself given rotation of the drum.

DESCRIPTION OF THE PREFERRED EMBODIMENTS

Figure 1:
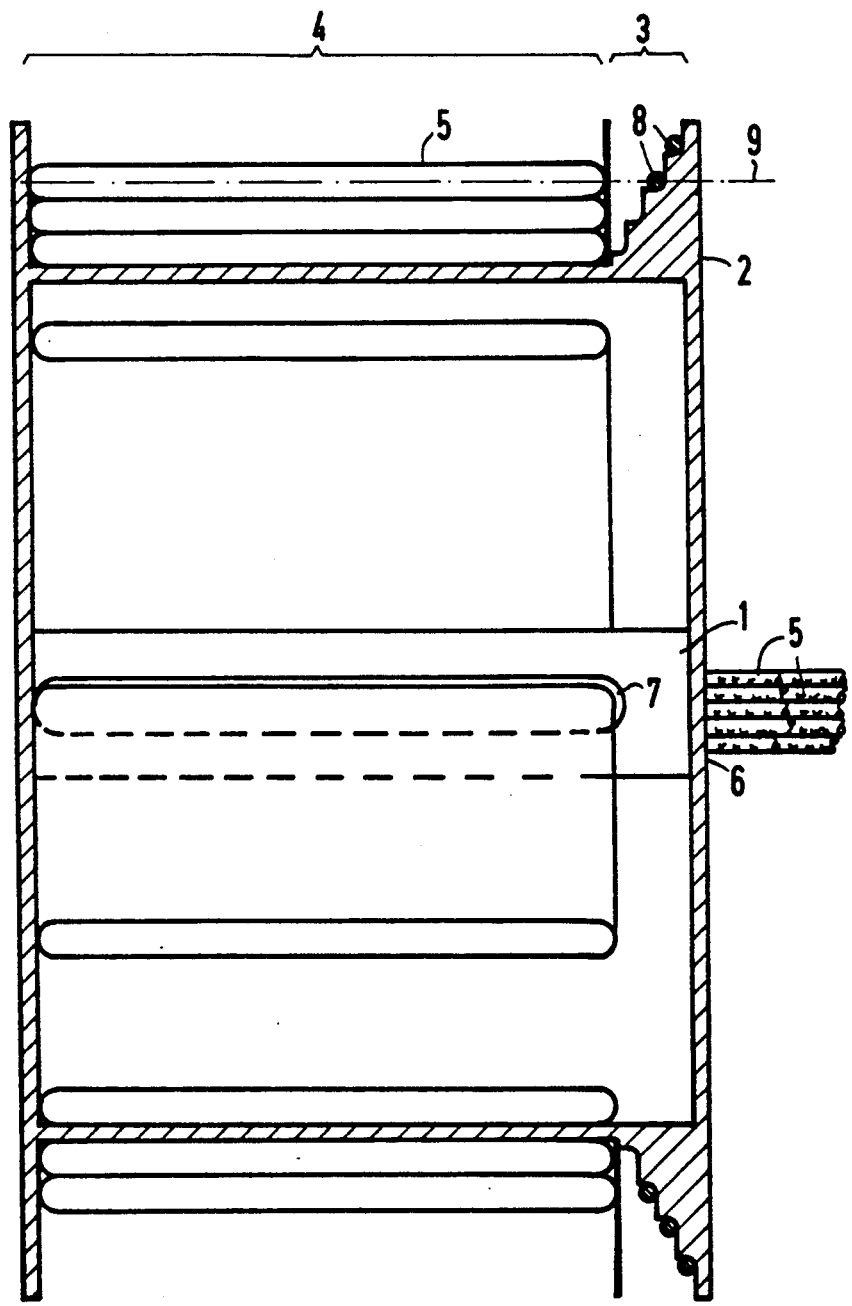
FIG. 1 is a sectional view of a mechanism for winding and unwinding a conductor and cable, constructed in accordance with the principles of the present invention.

A mechanism for accepting a conductor and a cable constructed in accordance with the principles of the present invention is shown in FIG. 1, which includes an inner, hollow, cylindrical drum 1 around which an outer, hollow, cylindrical drum 2 is rotatably seated. The outer drum 2 has a first width region 3 and a second width region 4. Preferably the respective jackets of the inner drum 1 and the outer drum 2 are helically fashioned with the "step" of the jackets being adapted to a turn of a conductor 5. The conductor 5 can thus be continuously wound onto the jackets (exteriors) of the drums 1 and 2. A first lengthwise region of the conductor 5 is conducted through a lateral opening 6 of the inner drum 1, and through an opening 7 of the jacket of the inner drum 1 into the region between the drums 1 and 2. The first lengthwise region of the conductor 5 is wound into a helix around the inner drum 1 and is conducted through an opening (not shown) of the jacket of the outer drum 2. The first region of the conductor 5 is mechanically fixed to the jacket of the inner drum 1 as well as to the jacket of the outer drum 2.

A second lengthwise region of the conductor 5, which adjoins the first region, is accepted by the second width region 4 of the outer drum 2, onto which it can be wound.

The first width region 3 of the outer drum 2 accepts a cable 8 which is received in the region 3 in a winding direction opposite to that of the conductor 5. If the diameter of the cable 8 is smaller than the height (diameter) of the conductor 5, the first width region 3 may be provided with a helical surface, with the pitch of the helix being such that a center line of the cable 8 and a center line of the conductor 5 both lie in a winding plane 9 of the conductor 5. When a tensile force is exerted on the conductor 5, it is thereby assured that the same length of the conductor 5 will be unwound from the second region 4 of the drum 2 as the length of cable 8 which is wound onto the helix of the first region 3. Conversely, when a tensile force is exerted on the cable 8, the cable 8 is unwound by the same length from the first region 3 as the conductor 5 is wound onto the second region 4. The conductor 5 need not consist of only a single conductor, but may be formed by a plurality of individual conductors. It may also be fashioned as a flat cable.

Figure 2:
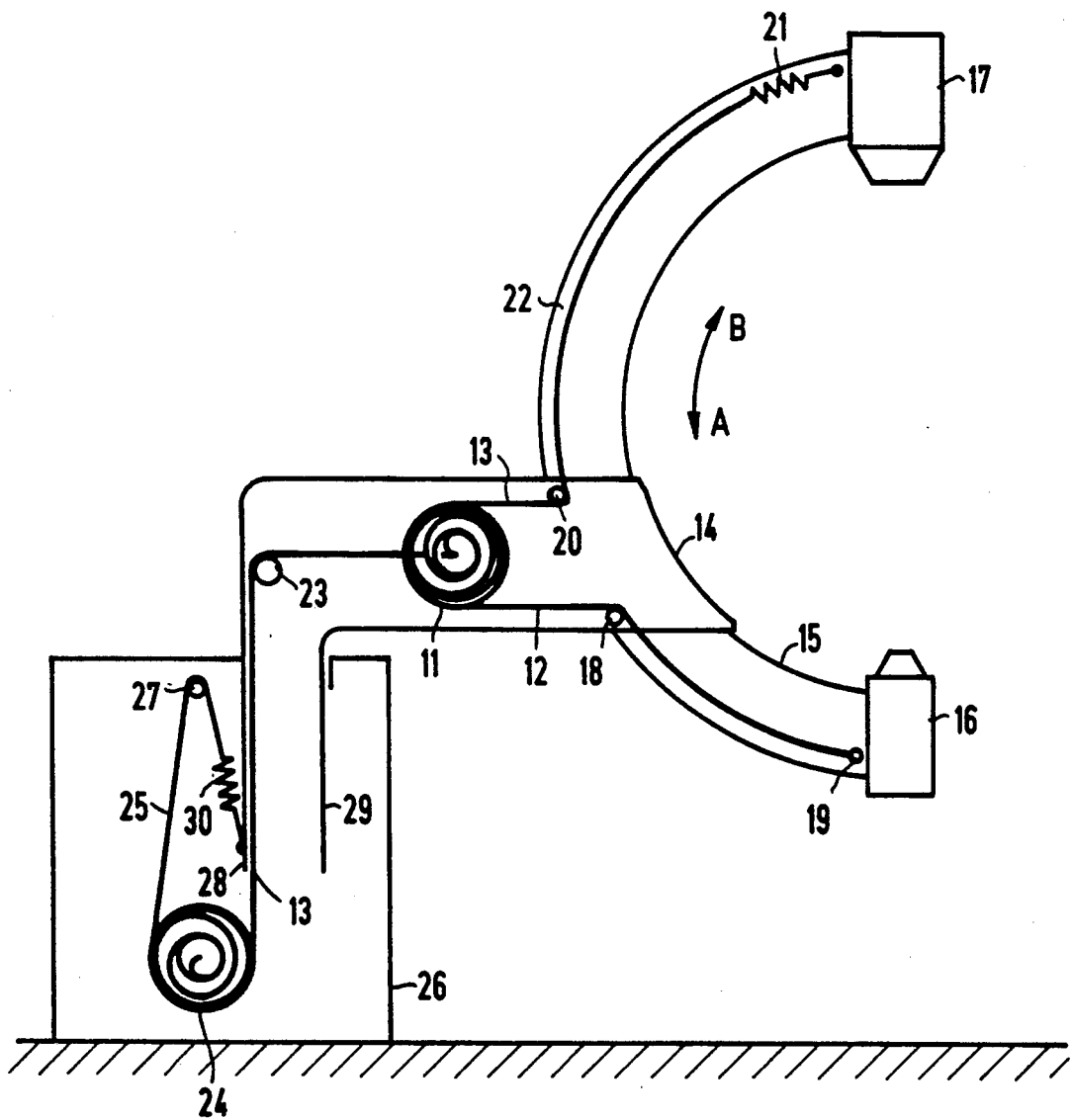
FIG. 2 is a side sectional view of a portable x-ray examination apparatus incorporating two examples of the mechanism of FIG. 1.

An example of an apparatus incorporating a mechanism 11, of the type shown in FIG. 1, is shown in FIG. 2. The mechanism 11 accepts a conductor 12 and a cable 13. In the exemplary embodiment of FIG. 2, the apparatus is an x-ray examination unit, which may be portable or fixed. The examination unit consists of a holder 14 for an arc 15, the arc 15 being movable with respect to the holder 14. The arc 15 is held by the holder 14 so as to be adjustable along its circumference. At its free ends, the arc 15 carries an x-radiator 16 and a radiation receiver 17, disposed opposite each other. The mechanism 11 is contained in the holder 14.

The second region of the conductor 12, which corresponds to aforementioned second region of the conductor 5 discussed in connection with FIG. 1, leads from the mechanism 11 via a first deflection roller 18 to an end of the arc 15 at which, for example, the x-radiator 16 is held. The conductor 12 is held by a mount 19 at this end. The cable 13 is conducted around a second deflection roller 20, and is secured via a spring element 21 to the other end of the arc 15 at which, for example, the radiation receiver 17 is held. The conductor 12 is provided for transmitting energy and signals between at least the radiation receiver 17 and other components (not shown) located remote from the arc 15. The cable 13 may be guided in a covered recess 22 of the arc 15.

When the arc 15 is displaced in the holder 14 in a direction A, a tensile force is exerted on the conductor 12, so that the conductor 12 is unwound from the outer drum of the mechanism 11. The rotation of this outer drum causes the cable 13 to be wound onto the outer drum. If, by contrast, the arc 15 is adjusted in a direction B, a tensile force is exerted on the cable 13, as a result of which the outer drum is rotated in the opposite direction. The cable 13 is thus unwound from this outer drum and the conductor 12 is wound onto the outer drum. An adjustment of the arc 15 which is neutral in force is thus insured. The spring element 21 exerts a constant tensile force on the cable 13, and thus on the conductor 12 as well, so that the conductor 12 is wound onto the outer drum with a slight pre-stress. This insures that the individual winding turns will lie tightly on each other.

The end of the conductor 12 emerging from the inner drum of the mechanism 11 is conducted via a further deflection roller 23 to the outer drum of a further mechanism 24, for the acceptance of the conductor 12 and of a cable 25. The mechanism 24 also corresponds to the mechanism described in FIG. 1, and is arranged in a base 26, in which the holder 14 is seated so as to be adjustable in height. The cable 25 is conducted via a deflection roller 27, and is connected via a spring element 30 to the lower end 28 of a vertical wall 29 of the holder 14. When the holder 14 is adjusted in height, the conductor 12 and the cable 25 are respectively wound onto and unwound from the outer drum of the further mechanism 24 (whether the cable 25 or the conductor 12 is wound or unwound from the outer drum being dependent on whether the holder 14 is being moved upwardly or downwardly).

The end of the conductor 12 emerging from the inner drum of the further mechanism 24 may, for example, be connected to a voltage source (not shown) and to an apparatus (not shown) for processing the signals of the radiation receiver 17. In this exemplary embodiment, the mechanism 24 could be arranged at a further vertical wall 29 of the holder 14, in which case the cable 25 would be secured in the upper region of the base 26, and the second region of the conductor 12 would be secured in the lower region of the base 26. A deflection roller for the cable 13 would then have to be provided, for example, at the lower end of the vertical wall 29.

Although modifications and changes may be suggested by those skilled in the art, it is the intention of the inventor to embody within the patent warranted hereon all changes and modifications as reasonably and properly come within the scope of his contribution to the art.

We claim as our invention:

1. An apparatus comprising:

an electrical conductor having one end mechanically attached at a first apparatus location;

a cable, separate from said conductor, having one end mechanically attached at a second apparatus location;

rotatable drum means entraining said conductor and said cable for respectively simultaneously winding said conductor and unwinding said cable in opposite directions and for simultaneously unwinding said conductor and winding said cable in opposite directions; and said cable having a diameter which is less than the height of a turn of said conductor on said drum means, and a first region of said drum means having a helix onto which said cable is wound having a pitch corresponding to said height of a turn of said conductor.

2. An apparatus as claimed in claim 1 wherein said drum means has a width, and wherein said cable is wound onto and unwound from a first width region of said drum means and said conductor is wound onto and unwound from a second width region of said drum means.

3. An apparatus as claimed in claim 1 wherein said cable has a diameter which is equal to the height of a turn of said conductor on said drum means.

4. An apparatus as claimed in claim 1 wherein said conductor is a flat cable.

5. An apparatus as claimed in claim 1 wherein said drum means comprises:

an inner, stationary, hollow, cylindrical drum having an exterior surface with an opening therein;

an outer, hollow, cylindrical drum rotatably seated around said inner drum and having an exterior surface with a width divided into first and second width regions and said exterior surface having an opening in said second width region;

said conductor extending through an interior of said inner drum and through said opening in the exterior surface of said inner drum into a region between said inner drum and said outer, and through said opening in said outer drum, and said conductor being mechanically fixed relative to said inner and said outer drum; and said cable being wound around said first width region of said outer drum so that, given rotation of the outer drum due to a tensile force acting on said cable, said conductor is wound onto said exterior surface of said inner drum and said second width region of said outer drum while said cable is unwound from said first width region, and given a tensile force acting on said conductor, said conductor is unwound from said second width region of said outer drum and said cable is wound onto said first width region of said outer drum.

6. An apparatus comprising:

a first unit and a second unit adjustable in position relative to said first unit;

an electrical conductor having one end mechanically attached at a first apparatus location on said second unit;

a cable, separate from said conductor, having one end mechanically attached at a second apparatus location on said second unit;

rotatable drum means entraining said conductor and said cable for respectively simultaneously winding said conductor and unwinding said cable in opposite directions and for simultaneously unwinding said conductor and winding said cable in opposite directions, so that when said second unit is moved in a first direction a tensile force is exerted on said conductor and when said second unit moves in a second, opposite direction a tensile force is exerted on said cable;

and wherein said second unit is an arc carrying an x-radiator and a radiation receiver at opposite free ends thereof, and wherein said first unit is a holder for said arc permitting adjustment of said arc along its circumference, and wherein said first apparatus location is disposed at one of said free ends of said arc, and said second apparatus location is disposed at an opposite free end of said arc.

7. An apparatus as claimed in claim 6 wherein said cable has a diameter which is less than the height of a turn of said conductor on said drum means, and wherein said first region of said drum means has a helix onto which said cable is wound having a pitch corresponding to the height of a turn of said conductor.

8. An apparatus as claimed in claim 6 wherein said cable is secured to said end of said arc at said second apparatus location via a spring element.

* * * * *